United States Patent [19]
Shigeto et al.

[11] Patent Number: 5,965,713
[45] Date of Patent: Oct. 12, 1999

[54] DYE LABELED PROTEIN CONJUGATE ITS PREPARING METHOD AND SENSOR USING THE SAME

[75] Inventors: Nobuyuki Shigeto; Jinsei Miyazaki; Hiroshi Nakayama, all of Osaka, Japan

[73] Assignee: Matsushita Electric Industrial Co., Ltd., Osaka, Japan

[21] Appl. No.: 08/745,337

[22] Filed: Nov. 8, 1996

[30] Foreign Application Priority Data

Nov. 9, 1995 [JP] Japan .................................. 7-290984

[51] Int. Cl.⁶ .......................... C07K 16/00; A61K 39/385
[52] U.S. Cl. .................. 530/402; 530/405; 530/387.1; 530/389.1; 530/391.3; 530/391.5; 530/391.9; 530/802; 530/861; 530/866; 424/193.1; 424/194.1; 436/91
[58] Field of Search ..................... 530/402, 405, 530/387.1, 389.1, 391.3, 391.5, 391.9, 802, 861, 866; 424/193.1, 194.1; 436/91

[56] References Cited

U.S. PATENT DOCUMENTS

| 5,378,634 | 1/1995 | Sigetoh et al. | 436/91 |
| 5,453,505 | 9/1995 | Lee et al. | 544/124 |

FOREIGN PATENT DOCUMENTS 0800083  8/1997  European Pat. Off. .
08259826  8/1996  Japan .

OTHER PUBLICATIONS

*Cytometry*, vol. 10, pp. 11–19, 1989.
*Chemical Abstract*, vol. 126, No. 3, p. 729, Ref. #33025K (JP–08,259,826, Aug. 10, 1996) 1997.
Ratnakar B. Mujumadar, et al., Cyanine Dye Labeling Reagents: Sulfoindoc–yanine Succinimidyl Esters, Bioconjugate Chemistry, vol. 4, No. 2, Mar./Apr. 1993.

*Primary Examiner*—Cecilia Tsang
*Assistant Examiner*—Abdez A. Mohamed
*Attorney, Agent, or Firm*—McDermott, Will & Emery

[57] ABSTRACT

It is intended to present a sensor capable of labeling with more dyes, applying the labeled protein in immunochromatography making use of antigen-antibody reaction, and having an excellent sensitivity. In a buffer, a protein and a first covalent bonding compound that can react with this protein are reacted to prepare a protein conjugate, then a cyanine labeling dye is added in the buffer containing the protein conjugate, and the protein conjugate and cyanine labeling dye are reacted to prepare a dye labeled protein conjugate. Alternatively, in a buffer solution, a protein and a cyanine labeling dye are reacted to prepare a dye labeled protein, then a first covalent bonding compound that can react with the protein is added in the buffer containing the dye labeled protein, and the dye labeled protein and first covalent bonding protein are reacted to prepare a dye labeled protein conjugate.

29 Claims, 4 Drawing Sheets

---

In a buffer, a protein and a first covalent bonding compound that can react with the protein are reacted.

↓

A protein conjugate is prepared.

↓

A cyanine labeling dye expressed in chemical formula 1 is added in the buffer containing the protein conjugate, and the protein conjugate and the cyanine labeling dye are reacted.

↓

A dye labeled protein conjugate is prepared.

```
In a buffer, a protein and a cyanine labeling dye expressed
in chemical formula 1 are reacted.
```
↓
```
A dye labeled protein is prepared.
```
↓
```
A first covalent bonding compound that can react with the
protein isadded in the buffer containing the dye labeled
protein, and the dye labeled protein and the first covalent
bonding compound are reacted.
```
↓
```
A dye labeled protein conjugate is prepared.
```

Fig. 3

```
┌─────────────────────────────────────────────────────────────┐
│ In a buffer, a first protein and a first covalent bonding   │
│ compound that can react with the first protein are reacted. │
└─────────────────────────────────────────────────────────────┘
                              │
                              ▼
┌─────────────────────────────────────────────────────────────┐
│ A first protein conjugate is prepared.                      │
└─────────────────────────────────────────────────────────────┘
                              │
                              ▼
┌─────────────────────────────────────────────────────────────┐
│ A second protein is added in the buffer containing the first│
│ protein conjugate, and the first protein conjugate and the  │
│ second protein are reacted.                                 │
└─────────────────────────────────────────────────────────────┘
                              │
                              ▼
┌─────────────────────────────────────────────────────────────┐
│ A second protein conjugate is prepared.                     │
└─────────────────────────────────────────────────────────────┘
                              │
                              ▼
┌─────────────────────────────────────────────────────────────┐
│ A cyanine labeling dye expressed in chemical formula 1 is   │
│ added in the buffer containing the second protein conjugate,│
│ and the second protein conjugate and the cyanine labeling   │
│ dye are reacted.                                            │
└─────────────────────────────────────────────────────────────┘
                              │
                              ▼
┌─────────────────────────────────────────────────────────────┐
│ A dye labeled protein conjugate is prepared.                │
└─────────────────────────────────────────────────────────────┘
```

Fig. 4

```
┌─────────────────────────────────────────────────────────────┐
│ In a buffer, a first protein and a first covalent bonding   │
│ compound that can react with the first protein are reacted. │
└─────────────────────────────────────────────────────────────┘
                              │
                              ▼
┌─────────────────────────────────────────────────────────────┐
│ A protein conjugate is prepared.                            │
└─────────────────────────────────────────────────────────────┘
          │
          │              ┌──────────────────────────────────┐
          │              │ A second protein and a cyanine   │
          │              │ labeling dye expressed in chemical│
          │              │ formula 1 are reacted in the     │
          │              │ buffer.                          │
          │              └──────────────────────────────────┘
          │                              │
          │                              ▼
          │              ┌──────────────────────────────────┐
          │              │ A dye labeled protein is prepared.│
          │              └──────────────────────────────────┘
          │                              │
          ▼                              ▼
┌─────────────────────────────────────────────────────────────┐
│ The protein conjugate and the dye labeled protein are mixed │
│ in the buffer, and the protein conjugate and the dye labeled│
│ protein are reacted.                                        │
└─────────────────────────────────────────────────────────────┘
                              │
                              ▼
┌─────────────────────────────────────────────────────────────┐
│ A dye labeled protein conjugate is prepared.                │
└─────────────────────────────────────────────────────────────┘
```

DYE LABELED PROTEIN CONJUGATE ITS PREPARING METHOD AND SENSOR USING THE SAME

BACKGROUND OF THE INVENTION

The present invention relates to a conjugate of protein labeled with a dye, its preparing method, and a sensor using the same.

Hitherto, the cyanine labeling dye having a highly reactive functional group has been often used in labeling of protein. In this case, the functional group of the labeling dye reacts with amino group or carboxyl group of protein, and about 20 to 50 molecules of labeling dye are bonded with one molecule of protein. Usually, protein contains hundreds to thousands of amino groups or carboxyl groups, but since the protein has a three-dimensional solid structure, only about 50 amino groups or carboxyl groups of them are estimated to participate in reaction. In the prior art, therefore, it was a limit to label one molecule of protein with about 50 molecules of dye.

It is hence an object of the invention (1) to enable to label with more dyes, (2) to apply labeled protein in immunochromatography utilizing antigen-antibody reaction, and (3) to obtain a sensor having an excellent sensitivity.

SUMMARY OF THE INVENTION

A dye labeled protein conjugate of the invention comprises:
  a protein conjugate, and
  a cyanine labeling dye covalently bonded to the protein as expressed in chemical formula 1. (In chemical formula 1, X denotes a halogen, M is hydrogen or alkaline metal, and n is an integer from 1 to 4.)

Chemical formula 1

(where X denotes a halogen, M is hydrogen or alkaline metal, and n is an integer from 1 to 4.)

Other dye labeled protein conjugate of the invention comprises:
  a protein conjugate group,
  a dye skeleton of cyanine labeling dye expressed in chemical formula 1, and
  a second covalent bonding compound group bonded between the protein conjugate group and dye skeleton.

A sensor of the invention composes the dye labeled protein conjugate.

A method of preparing a dye labeled protein conjugate of the invention comprises:
  (1) a step of reacting a protein with a first covalent bonding compound that can react with the protein in a buffer, thereby producing a protein conjugate, and
  (2) a step of adding a cyanine labeling dye expressed in chemical formula 1 in the buffer containing the protein conjugate, and reacting the protein conjugate with the cyanine labeling dye.

Other method of preparing a dye labeled protein conjugate of the invention comprises:
  (1) a step of reacting a protein with a cyanine labeling dye expressed in chemical formula 1 in a buffer, thereby producing a dye labeled protein, and
  (2) a step of adding a first covalent bonding compound that can react with the protein in the buffer containing the dye labeled protein, and reacting the dye labeled protein with the first covalent bonding compound.

A different method of preparing a dye labeled protein conjugate of the invention comprises:
  (1) a step of reacting a first protein with a first covalent bonding compound that can react with the first protein in a buffer, thereby producing a first protein conjugate,
  (2) a step of adding a second protein in the buffer containing the first protein conjugate, and reacting the first protein conjugate with the second protein, thereby producing a second protein conjugate, and
  (3) a step of adding a cyanine labeling dye expressed in chemical formula 1 in the buffer containing the second protein conjugate, and reacting the second protein conjugate with the cyanine labeling dye.

A further different method of preparing a dye labeled protein conjugate of the invention comprises:
  (1) a step of reacting a first protein with a first covalent bonding compound that can react with the first protein in a buffer, thereby producing a protein conjugate,
  (2) a step of reacting a second protein with a cyanine labeling dye expressed in chemical formula 1 in the buffer, thereby producing a dye labeled protein, and
  (3) a step of mixing the protein conjugate and the dye labeled protein in the buffer, and reacting the protein conjugate with the dye labeled protein.

In the above constitutions, as the protein, mouse immunoglobulin G or bovine serum albumin is particularly preferred. As the covalent bonding chemical, succinimidyl pyridyl dithiopropionate is particularly preferred. As the buffer, phosphate buffer is particularly preferred.

By the dye labeled protein conjugate and its preparing method of the invention, the number of dye molecules bonded to one molecule of protein can be spuriously increased about 10 times more than in the prior art. Therefore, the sensor applying this dye labeled protein conjugate in immunochromatography can obtain an extremely high sensitivity as compared with the sensor fabricated by the conventional manner.

Moreover, by the method of preparing dye labeled protein conjugate of the invention, one molecule of protein can be spuriously labeled with millions of dye molecules, which was impossible previously, and hence a novel method of preparing dye labeled protein conjugate can be presented.

DESCRIPTION OF THE PREFERRED EMBODIMENTS

Embodiments of the invention are described below.

Figure 1:
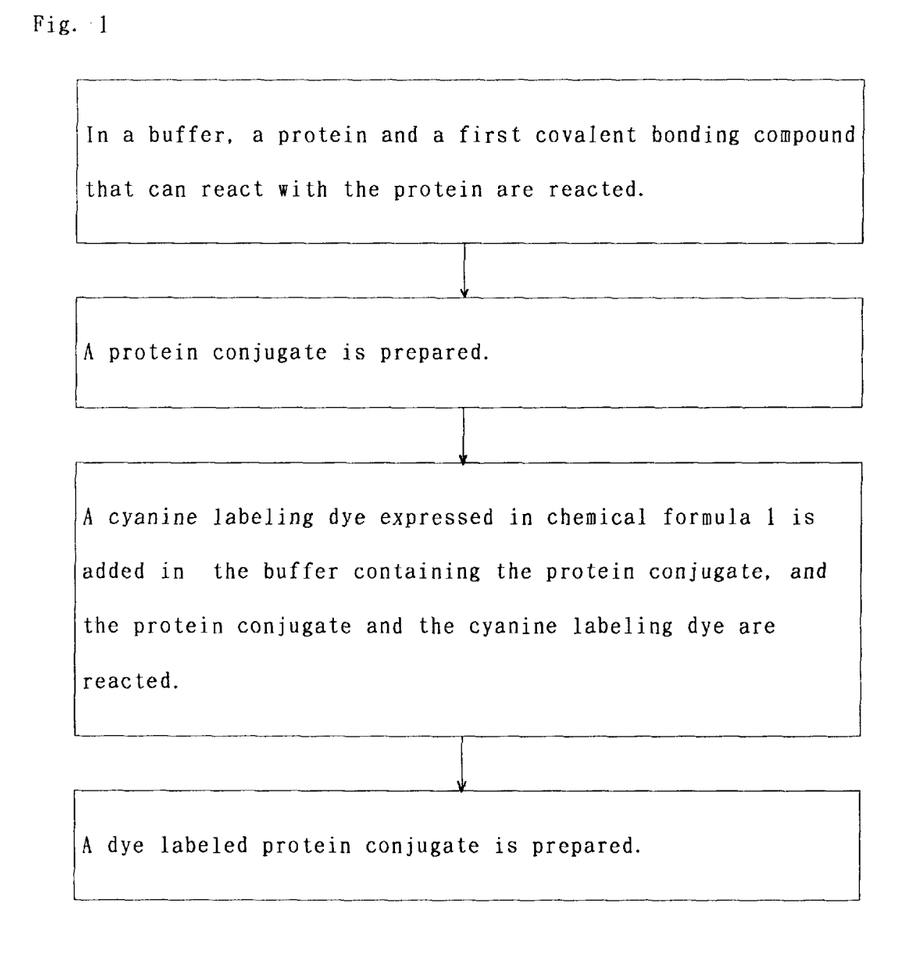
FIG. 1 is a preparation process diagram in an embodiment of a method of preparing dye labeled protein conjugate of the invention.

A process diagram showing an embodiment of a method of preparing dye labeled protein conjugate of the invention is shown in FIG. 1. In FIG. 1, first (1) a protein and a first covalent bonding compound that can react with this protein are reacted in a buffer, and a protein conjugate is prepared. Then (2) a cyanine labeling dye expressed in chemical formula 1 is added in the buffer containing the protein conjugate, and the protein conjugate and the cyanine labeling dye are reacted. Thus, a dye labeled protein conjugate is prepared.

Figure 2:
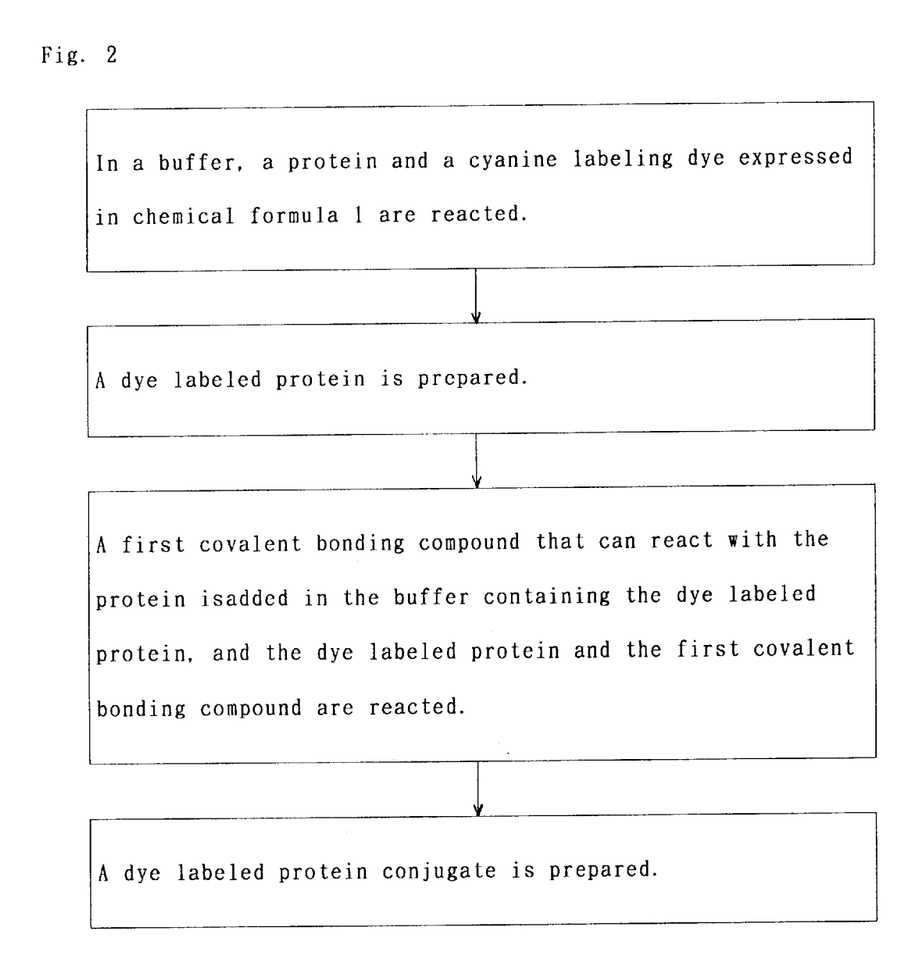
FIG. 2 is a preparation process diagram in other embodiment of a method of preparing dye labeled protein conjugate of the invention.

A process diagram showing other embodiment of a method of preparing dye labeled protein conjugate of the invention is shown in FIG. 2. In FIG. 2, first (1) a protein and a cyanine labeling dye expressed in chemical formula 1 are reacted in a buffer, and a dye labeled protein is prepared. Then (2) a first covalent bonding compound that can react with the protein is added in the buffer containing the dye labeled protein, and the dye labeled protein and first covalent bonding compound are reacted. Thus, a dye labeled protein conjugate is prepared.

As the buffer, phosphate buffer saline (PBS) is preferred. As the first covalent bonding compound, succinimidyl pyridyl dithiopropionate (SPDP) is preferred. As the protein, mouse immunoglobulin (IGG) or bovine serum albumin (BSA) is preferred.

Figure 3:
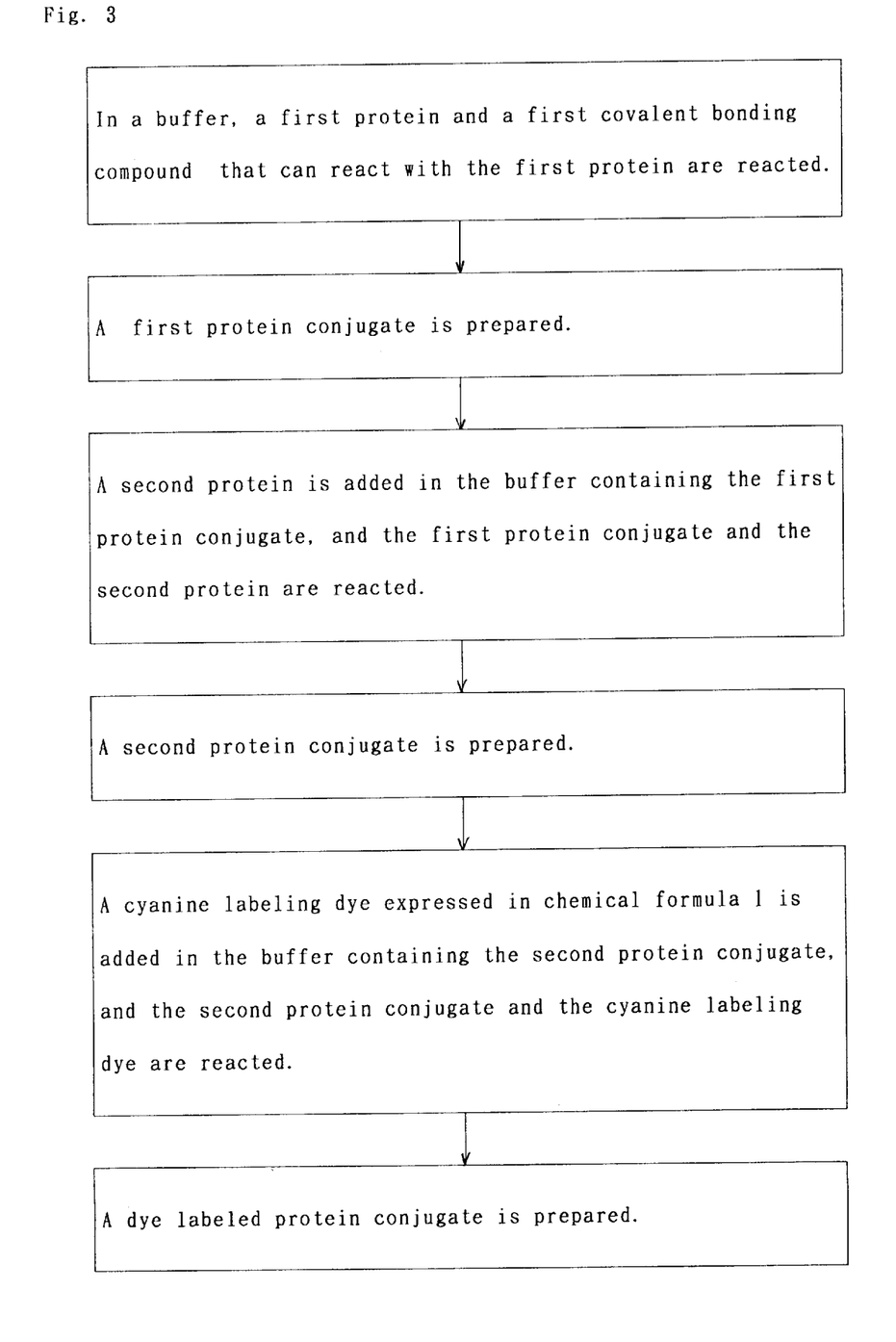
FIG. 3 is a preparation process diagram in a different embodiment of a method of preparing dye labeled protein conjugate of the invention.

A process diagram showing a different embodiment of a method of preparing dye labeled protein conjugate of the invention is shown in FIG. 3. In FIG. 3, first (1) a first protein and a first covalent bonding compound that can react with the first protein are reacted in a buffer, and a first protein conjugate is prepared. Next (2) a second protein is added in the buffer containing the first protein conjugate, and the first protein conjugate and the second protein are reacted, and a second protein conjugate is prepared. Then (3) a cyanine labeling dye expressed in chemical formula 1 is added in the buffer containing the second protein conjugate, and the second protein conjugate and the cyanine labeling dye are reacted. Thus, a dye labeled protein conjugate is prepared.

This embodiment is further described below. In the PBS of mouse IGG as first protein, SPDP is added to label with pyridyl thio. In this solution, a second protein (for example, BSA) preliminarily reduced in dithiothreitol (DDT) is added by 20 to 100 equivalent moles, and stirred for about 12 hours at about 40 to 30° C. Afterwards, a PBS of cyanine labeling dye expressed in chemical formula 1 is added, and stirred for about 12 hours at about 40 to 30° C. Thus, a dye labeled protein conjugate is prepared.

Figure 4:
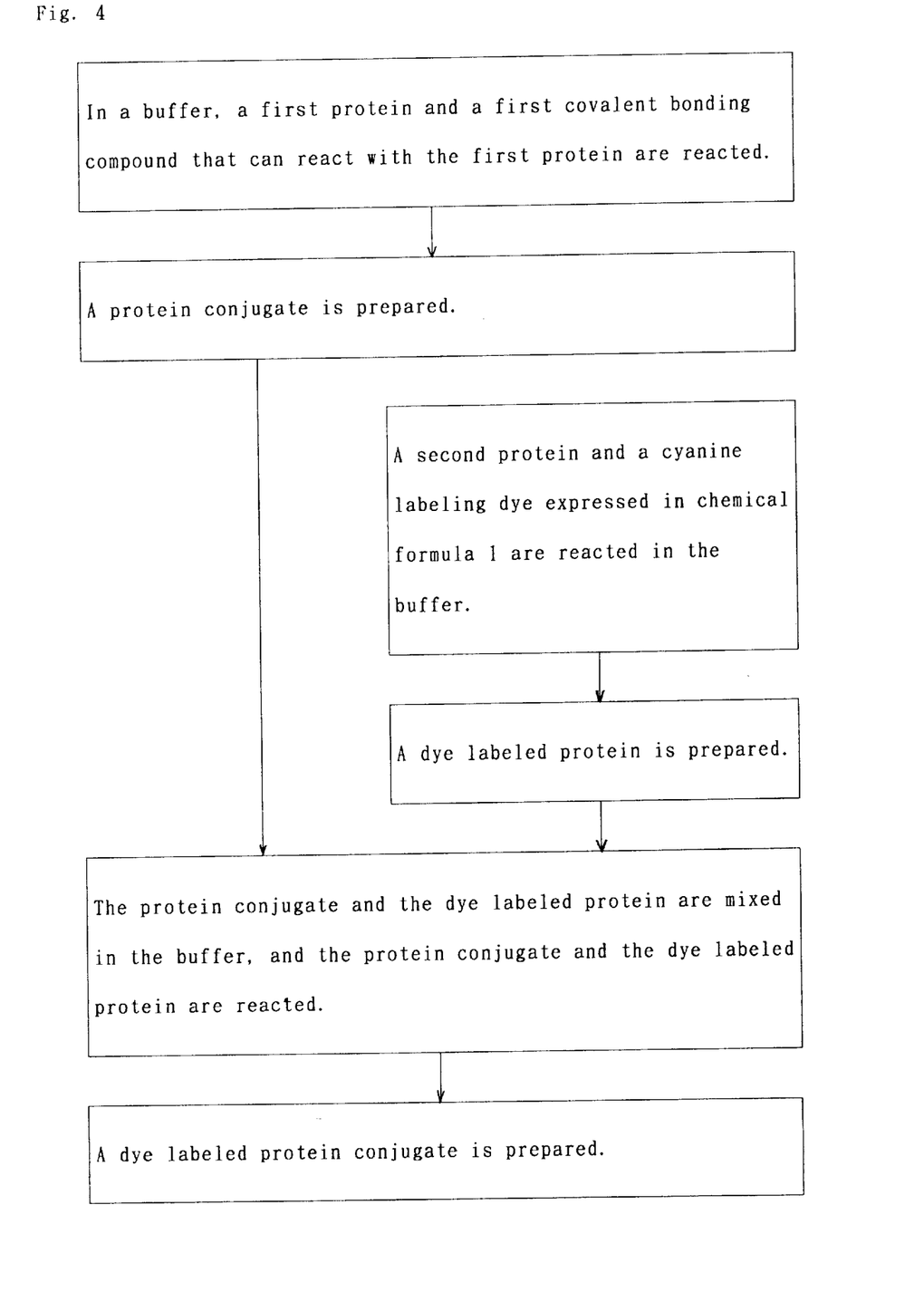
FIG. 4 is a preparation process diagram in a further different embodiment of a method of preparing dye labeled protein conjugate of the invention.

A process diagram showing a further different embodiment of a method of preparing dye labeled protein conjugate of the invention is shown in FIG. 4. In FIG. 4, first (1) a first protein and a first covalent bonding compound that can react with the first protein area reacted in a buffer, and a protein conjugate is prepared. Next (2) a second protein and a cyanine labeling dye expressed in chemical formula 1 are reacted in the buffer, and a dye labeled protein is prepared. Then (3) a protein conjugate and the dye labeled protein are mixed in the buffer, and the protein conjugate and the dye labeled protein are reacted. Thus, a dye labeled protein conjugate is prepared.

This embodiment is further described below. In the PBS of BSA as first protein, a PBS of cyanine labeling dye expressed in chemical formula 1 is added, and stirred for about 12 hours at about 40 to 30° C. It is then reduced in DTT. A preliminarily pyridyl thio labeled second protein (for example, mouse IGG) is added therein and stirred for about 12 hours at about 40 to 30° C. Thus, a dye labeled protein conjugate is prepared.

In the compound expressed in chemical formula 1, halogen X is, for example, fluorine, chlorine, bromine or iodine, and M is hydrogen, lithium, sodium or potassium.

The invention is further described below by referring to specific embodiments. In the compound expressed in chemical formula 1 of the embodiment, X is iodine, M is potassium, and number of carbon atoms n is 2. The protein is IGG and BSA. The cyanine labeling dye expressed in chemical formula 1 is abbreviated as SLIC3.

(Embodiment 1)

(1) Labeling of IGG with SPDP

In 2 ml of PBS, 5 mg ($3.3 \times 10^{-5}$ mmol) of IGG was dissolved, and while stirring at room temperature, 0.1 ml of ethanol solution of 0.52 mg ($1.67 \times 10^{-3}$ mmol) of SPDP was dropped. After stirring for 30 minutes at room temperature, it was subjected to gel filtration by using Sephadex G25M column (Pharmacia). In this way, about 6 ml of PBS of SPDP labeled IGG (IGG-SPDP) was obtained. The concentration and number of bonding molecules of SPDP of the obtained solution were calculated as follows. From the obtained solution, 0.5 ml was sampled, and the absorbance was measured at 280 nm. The absorbance was 1.25.

In this solution, 0.025 ml of 100 mM DTT aqueous solution was added, and let stand for 1 minute, and the absorbance at 343 nm was measured. The absorbance was 0.39. Since IGG is not absorbed at 343 nm, the observed absorption at 343 nm is derived from the thiopyridone reduced by DTT reduction. This released thiopyridone is a reduced product of pyridyl thio group of SPDP, and its concentration is equal to the concentration of SPDP bonded with the antibody. Therefore, the SPDP concentration [SPDP] can be determined as follows. Herein, the molar extinction coefficient of thiopyridone at 343 nm is supposed to be $8.08 \times 10^3$.

[SPDP]=$0.39/(8.08 \times 10^3)$=$4.83 \times 10^{-5}$(M)

The observed absorption at 280 nm is derived from IGG, but since the bonded SPDP is also absorbed at 280 nm, subtracting its effect, the IGG concentration [IGG] is determined as follows. Herein, the absorbance at 280 nm attributable to IGG is supposed to be $Ab_{280,IGG}$, the molar extinction coefficient of SPDP at 280 nm to be $5.1 \times 10^3$, and the molar extinction coefficient of IGG at 280 nm to be $2.10 \times 10^5$.

$Ab_{280,IGG}$=$1.25-(4.83 \times 10^{-5} \times 5.1 \times 10^3)$=$1.00$

[IGG]=$1.00/(2.10 \times 10^5)$=$4.78 \times 10^{-6}$ M

Therefore, the number of molecules of SPDP bonded with one molecule of IGG is as follows.

[SPDP]/[IGG]=$4.83 \times 10^{-5}/4.78 \times 10^{-6}$=10.1 (molecules)

(2) Reduction of BSA in DTT

In 10 ml of PBS, 110 mg of BSA was dissolved, and 77 mg of DTT dissolved in 1 ml of PBS was added, and stirred for 15 minutes at room temperature. By quickly presented for gel filtration in Sephadex G25M column, about 24 ml of PBS of BSA (SH-free) was obtained.

(3) Preparation of protein conjugate (IGG-SPDP-BSA)

The obtained BSA (SH-free) solution was promptly mixed with the PBS (6 ml) of IGG-SPDP obtained above, and was let stand for 20 hours at 4° C. To remove unreacted BSA, it was dialyzed in 20 L (5 L×4) of PBS·Az, and about 25 ml of PBS of IGG-SPDP-BSA was obtained.

(4) Labeling of protein conjugate (IGG-SPDP-BSA) with dye

In the obtained IGG-SPDP-BSA solution (total protein supposed to be $3.18 \times 10^{-4}$ mmol), 131.1 mg (400 times equivalent of total protein) of a dye solution expressed in chemical formula 1 (hereinafter called SLIC3) dissolved in 1 ml of PBS was dropped slowly. After letting stand for 20 hours at 4° C., to remove unreacted dye molecules, it was dialyzed in 20 L of PBS·Az, and about 26 ml of PBS of SLIC3 labeled protein conjugate was obtained.

Of the obtained SLIC3 labeled protein conjugate, the number of molecules of SLIC3 per one molecule of IGG was calculated as follows. The absorbance of the obtained solution at 550 nm was measured. The absorbance was 77.1. Since the IGG-SPDP-BSA is not absorbed at 550 nm, the observed absorption is derived from the bonded SLIC3. Therefore, the SLIC3 concentration [SLIC3] can be determined as follows. Herein, the molar extinction coefficient of SLIC3 at 550 nm is supposed to be $8.55 \times 10^4$.

$$[SLIC3] = 77.1/8.55 \times 10^4 = 9.02 \times 10^{-4} (M)$$

Supposing the IGG concentration [IGG] in the solution to be $1.06 \times 10^{-6}$ M (assuming there is no loss of IGG in each step after SPDP labeling), the number of molecules of SLIC3 per 1 molecule of IGG is as follows.

$$[SLIC3]/[IGG] = 9.02 \times 10^{-4}/1.06 \times 10^{-6} = 850.9 \text{ (molecules)}$$

(Embodiment 2)

(1) Labeling of IGG with SPDP

According to the method presented in embodiment 1, IGG was labeled with SPDP. The total volume was 6 ml, the IGG concentration was $4.10 \times 10^{-6}$ M, and the number of molecules of SPDP per 1 molecule of IGG was 11.5.

(2) Preparation of BSA-SLIC3

In 10 ml of PBS, 110 mg ($1.62 \times 10^{-3}$ mmol) of BSA was dissolved, and while stirring at room temperature, 171.7 mg (0.162 mmol, 100 equivalent) of SLIC3 dissolved in 1 ml of PBS was dropped slowly. After stirring overnight at 4° C., it was dialyzed in 20 L (5 L×4) of PBS·Az, and 13 ml of PBS of SLIC3 labeled BSA was obtained. The concentration of the solution, and the number of molecules of SLIC3 bonded with one molecule of BSA were calculated as follows. The absorbance of the obtained solution at 280 nm and 550 nm was measured. The absorbance was respectively 9.7 and 55.3. Since BSA is not absorbed at 550 nm, the absorption observed at 550nm is derived from SLIC3 bonded with BSA. Therefore, the SLIC3 concentration [SLIC3] can be determined as follows. Herein, the molar extinction coefficient of SLIC3 at 550 nm is supposed to be $8.55 \times 10^4$.

$$[SLIC3] = 55.3/8.55 \times 10^4 = 6.46 \times 10^{-4} (M)$$

The observed absorption at 280 nm is derived from BSA, but since the bonded SLIC3 is also absorbed at 280 nm, subtracting its effect, the BSA concentration [BSA] is determined as follows. Herein, the absorbance at 280 nm attributable to BSA is supposed to be $Ab_{280,BSA}$, the molar extinction coefficient of SLIC3 at 280 nm to be $9.8 \times 10^3$, and the molar extinction coefficient of BSA at 280 nm to be $4.36 \times 10^4$.

$$Ab_{280,BSA} = 9.7 - (6.46 \times 10^{-4} \times 9.8 \times 10^3) = 3.37$$

$$[BSA] = 3.37/4.36 \times 10^4 = 7.72 \times 10^{-5} (M)$$

Therefore, the number of molecules of SLIC3 bonded with one molecule of BSA is as follows.

$$[SLIC3]/[BSA] = 6.46 \times 10^{-4}/7.72 \times 10^{-5} = 8.4 \text{ (molecules)}$$

(3) Reduction of BSA-SLIC3 in DTT

In the above BSA-SLIC3 solution (110 mg, 13 ml), 100 mg of DTT dissolved in 1 ml of PBS (final concentration 50 mM) was added, and stirred for 15 minutes at room temperature. By quickly presented for gel filtration in Sephadex G25M column, about 24 ml of BSA-SLIC3 (SH-free) was obtained.

(4) Preparation of dye labeled protein conjugate

The obtained BSA-SLIC3 (SH-free) solution, and the above SPDP labeled IGG solution were mixed, and stirred overnight at 4° C., and it was dialyzed in 20 L of PBS·Az, and the unreacted BSA-SLIC3 was removed. About 30 ml of PBS of dye labeled protein conjugate was obtained.

Of the obtained SLIC3 labeled protein conjugate, the number of molecules of SLIC3 per one molecule of IGG was calculated as follows. The absorbance of the obtained solution at 550 nm was measured. The absorbance was 29.5. Since the IGG is not absorbed at 550 nm, the observed absorption is derived from the SLIC3 bonded to BSA. Therefore, the SLIC3 concentration [SLIC3] can be determined as follows. Herein, the molar extinction coefficient of SLIC3 at 550 nm is supposed to be $8.55 \times 10^4$.

$$[SLIC3] = 29.5/8.55 \times 10^4 = 3.45 \times 10^4 (M)$$

Supposing the IGG concentration [IGG] in the solution to be $8.20 \times 10^{-7}$ M (assuming there is no loss of IGG in each step after SPDP labeling), the number of molecules of SLIC3 per 1 molecule of IGG is as follows.

$$[SLIC3]/[IGG] = 3.45 \times 10^{-4}/8.20 \times 10^{-7} = 420.7 \text{ (molecules)}$$

As described herein, the dye labeled protein conjugate of the invention has the number of molecules of dye bonded with one molecule of protein increased spuriously about 10 times as many as in the conventional method. Therefore, by using this dye labeled protein in the sensor making use of immunochromatography, a sensor of a very high sensitivity as compared with the case of using the labeling protein prepared in the conventional method can be fabricated.

Besides, according to the method of preparing dye labeled protein conjugate of the invention, the SPDP is used after (a) preparing a protein conjugate by using SPDP in PBS, and adding and stirring the cyanine labeling dye expressed in chemical formula 1, or (b) mixing a protein and a cyanine labeling dye expressed in chemical formula 1 in PBS, and preparing a dye labeled protein. According to this method, a dye labeled substance can be prepared, and therefore a new method of preparing a dye labeled protein conjugate can be presented.

What is claimed is:

1. A dye labeled protein conjugate comprising:

a first protein and a covalent bonding compound, and a cyanine labeling dye covalently bonded to aid protein conjugate as expressed in chemical formula 1,

[Chemical formula 1]

where X denotes a halogen, M is hydrogen or alkaline metal, and n is an integer from 1 to 4.

2. A sensor for immunochromatography possessing the dye labeled protein conjugate of claim 1.

3. A dye labeled protein conjugate of claim 1, wherein said protein conjugate further comprises a second protein, wherein said covalent bonding compound is bonded between said first protein and said second protein.

4. A dye labeled protein conjugate of claim 3, wherein said covalent bonding compound comprises a first functional group that can react with said first protein, and a second functional group that can react with said second protein.

5. A dye labeled protein conjugate of claim 3, wherein said first protein and said second protein are selected from the group consisting of mouse IGG and bovine serum albumin.

6. A dye labeled protein conjugate of claim 3, wherein said covalent bonding compound comprises a succinimidyl pyridyl dithiopropionate group.

7. A dye labeled protein conjugate comprising:
   a first protein,
   a first covalent bonding compound bonded to said first protein,
   a cyanine labeling dye expressed in chemical formula 1,
   a second covalent bonding compound bonded between said first protein and a dye skeleton as expressed in chemical formula 1,

[Chemical formula 1]

where X denotes a halogen, M is hydrogen or alkaline metal, and n is an integer from 1 to 4.

8. A dye labeled protein conjugate of claim 7, wherein said second covalent bonding compound comprises a first functional group that can react with an amino group of said protein, and a second functional group that can react with a succinimidyl group of said cyanine labeling dye.

9. A dye labeled protein conjugate of claim 7, wherein said second covalent bonding compound comprises a succinimidyl pyridyl dithiopropionate group.

10. A dye labeled protein conjugate of claim 7, wherein said protein conjugate further comprises a second protein, wherein said first covalent bonding compound is bonded between said first protein and said second protein, and said second covalent bonding compound possesses a first functional group that can react with an amino group of said first protein or said second protein, and a second functional group that can react with a succinimidyl group of said cyanine labeling dye.

11. A dye labeled protein conjugate of claim 7, wherein said dye labeled protein conjugate is selected from the group consisting of mouse IGG and bovine serum albumin.

12. A dye labeled protein conjugate of claim 7, wherein said protein conjugate further comprises a second protein, wherein said first covalent bonding compound is bonded between said first protein and said second protein.

13. A dye labeled protein conjugate of claim 12, wherein each one of said first protein and second protein is at least one of mouse IGG and bovine serum albumin.

14. A dye labeled: protein conjugate of claim 12, wherein said first covalent bonding compound comprises a first functional group that can react with said first protein, and a second functional group that can react with said second protein.

15. A dye labeled protein conjugate of claim 12, wherein said first covalent bonding compound comprises a succinimidyl pyridyl dithiopropionate group.

16. A method of preparing a dye labeled protein conjugate comprising:
   (1) a step of reacting a protein with a first covalent bonding compound that can react with said protein in a buffer, thereby producing a protein conjugate, and
   (2) a step of adding a cyanine labeling dye expressed in chemical formula 1 in said buffer containing said protein conjugate, and reacting said protein conjugate with said cyanine labeling dye as expressed in chemical formula 1, where X denotes a halogen, M is hydrogen or alkaline metal, and n is an integer from 1 to 4.

17. A method of preparing a dye labeled protein conjugate of claim 16, wherein said buffer is a phosphate buffer saline.

18. A method of preparing a dye labeled protein conjugate of claim 16, wherein said first covalent bonding compound is succinimidyl pyridyl dithiopropionate.

19. A method of preparing a dye labeled protein conjugate comprising:
   (1) a step of reacting a protein with a cyanine labeling dye expressed in chemical formula 1 in a buffer, thereby producing a dye labeled protein, and
   (2) a step of adding a first covalent bonding compound that can react with said protein in said buffer containing said dye labeled protein, and reacting said dye labeled protein with said first covalent bonding compound as expressed in chemical formula 1, where X donates a halogen, M is hydrogen or alkaline metal, and n is an integer from 1 to 4.

20. A method of preparing a dye labeled protein conjugate of claim 19, wherein said buffer is a phosphate buffer saline.

21. A method of preparing a dye labeled protein conjugate of claim 19, wherein said first covalent bonding compound is succinimidyl pyridyl dithiopropionate.

22. A method of preparing a dye labeled protein conjugate comprising:

(1) a step of reacting a first protein with a first covalent bonding compound that can react with said first protein in a buffer (2) a step of adding a second protein in said buffer containing said first protein bonded to said first covalent bonding compound and reacting said first protein bonded to said first covalent bonding compound with said second protein, and (3) a step of adding a cyanine labeling dye expressed in chemical formula 1 in said buffer containing said first protein and said second proteins bonded to said first covalent bonding compound and reacting said first protein and said second protein bonded to said first covalent bonding compound with said cyanine labeling dye as expressed in chemical formula 1,

[Chemical formula 1]

where X denotes a halogen, M is hydrogen or alkaline metal, and n is an integer from 1 to 4.

23. A method of preparing a dye labeled protein conjugate of claim 22, wherein said buffer is a phosphate buffer saline.

24. A method of preparing a dye labeled protein conjugate of claim 22, wherein said first covalent bonding compound is succinimidyl pyridyl dithiopropionate.

25. A method of preparing a dye labeled protein conjugate of claim 22, wherein said first protein is mouse IGG, and said second protein is bovine serum albumin.

26. A method of preparing a dye labeled protein conjugate comprising:

(1) a step of reacting a first protein with a first covalent bonding compound that can react with said first protein in a buffer, (2) a step of reacting a second protein with a cyanine labeling dye expressed in chemical formula 1 in said buffer, thereby producing a dye labeled protein, and (3) a step of nixing said first protein bonded to said first covalent bonding compound and said dye labeled second protein in said buffer, and reacting said first protein bonded to said first covalent bonding compound with said dye labeled second protein as expressed in chemical formula 1,

[Chemical formula 1]

where X denotes a halogen, M is hydrogen or alkaline metal, and n is an integer from 1 to 4.

27. A method of preparing a dye labeled protein conjugate of claim 26, wherein said buffer is a phosphate buffer saline.

28. A method of preparing a dye labeled protein conjugate of claim 26, wherein said first covalent bonding compound is succinimidyl pyridyl dithiopropionate.

29. A method of preparing a dye labeled protein conjugate of claim 26, wherein said first protein is mouse IGG, and said second protein is bovine serum albumin.

* * * * *

UNITED STATES PATENT AND TRADEMARK OFFICE
CERTIFICATE OF CORRECTION

PATENT NO. : 5,965,713  
DATED : October 12, 1999  
INVENTOR(S) : Nobuyuki Shigetou et al.

It is certified that error appears in the above-identified patent and that said Letters Patent is hereby corrected as shown below:

<u>Title page,</u>  
Item [75], Inventors, change "Shigeto" to -- Shigetou --.

Signed and Sealed this

Fifth Day of February, 2002

Attest:

Attesting Officer

JAMES E. ROGAN  
Director of the United States Patent and Trademark Office